United States Patent [19]

Passariello

[11] Patent Number: 4,459,369

[45] Date of Patent: Jul. 10, 1984

[54] CATALYST FOR THE SYNTHESIS OF OXYGENATED ORGANIC COMPOUNDS AND PROCESS FOR ITS MANUFACTURE

[75] Inventor: Attilio Passariello, Tivoli, Italy

[73] Assignee: Ammonia Casale S.A., Lugano, Switzerland

[21] Appl. No.: 438,293

[22] Filed: Nov. 1, 1982

[30] Foreign Application Priority Data

Nov. 6, 1981 [CH] Switzerland ............... 7095/81

[51] Int. Cl.³ ............... B01J 21/06; B01J 23/02; B01J 23/04; B01J 23/72
[52] U.S. Cl. ............... 502/306; 502/309; 502/328; 502/331; 518/713
[58] Field of Search ............... 252/467, 468, 469, 471, 252/475, 476; 518/713; 502/306, 309, 328, 331

[56] References Cited

U.S. PATENT DOCUMENTS 4,181,630 1/1980 Baglin et al. ............... 252/476

FOREIGN PATENT DOCUMENTS 42-11733 4/1967 Japan ............... 252/467
53-142396 12/1978 Japan ............... 252/469
326977 3/1972 U.S.S.R. ............... 252/471

Primary Examiner—W. J. Shine
Attorney, Agent, or Firm—Holman & Stern

[57] ABSTRACT

Catalyst for heterogeneous synthesis and more particularly for the preparation of oxygenated compounds from synthesis gas (substantially $H_2$ and CO and $CO_2$), based on the general formula:

$$CuTi_aM_bA_c$$

in which M is at least one metal selected from the group consisting of chrome, manganese, cobalt, molybdenum, rhodium platinum and iron, A is an alkali or alkaline earth metal, a is comprised within 0.1 and 0.5 and b and c may vary between 0 and 0.2.

Application of these catalysts for the preparation of higher alcohol mixtures (fuel grade) $C_1$-$C_4$ when b and c are zero, and $C_1$-$C_4$ (for about 50%) and $C_5$-$C_{10}$ (for the other 50%) when b and c are other than zero.

8 Claims, No Drawings

CATALYST FOR THE SYNTHESIS OF OXYGENATED ORGANIC COMPOUNDS AND PROCESS FOR ITS MANUFACTURE

DESCRIPTION

This invention concerns a catalyst for heterogeneous synthesis, consisting, in the non-reduced state, of metal oxides. The invention concerns also a process for the preparation of oxygenated organic compounds and more particularly of fuel grade alcohol mixtures.

The need for efficient catalytic processes for the preparation of alcohol mixtures to be used as or with fuel, starting from synthesis gas consisting substantially of hydrogen, carbon monoxide and carbon dioxide (with or without the addition of small amounts of $CH_4$ and $N_2$) has always been keenly felt.

To fulfil this need, numerous processes have been put forward which can be schematically divided into three groups:

(1) Processes and catalysts deriving from those used for the synthesis of hydrocarbons (Fischer-Tropsch, Synthol, Isosynthesis, Synol).
(2) Catalysts used for methanol synthesis, suitably modified.
(3) Synthesis from CO, $H_2$ and olefine (oxosynthesis).

In Chapter 3, "Direct catalytic synthesis of higher alcohols from carbon monoxide and hydrogen" of "Catalysis", Volume 5, Natta, Colombo and Pasquon, besides reviewing its history, thermodynamic considerations and reactions, describe also and especially all experimental catalysts as well as those most commonly used. The Chapter in question ends with as many as 66 bibliographic references and provides, therefore, a complete survey of this important field.

More particularly, the various types of catalyst are substantially classified as follows:

(I) Catalysts based on ZnO with alkaline promoters; (II) catalysts based on ZnO and $Cr_2O_3$ with alkaline promoters; (III) catalysts containing Zn, Mn, and Cr oxides activated with alkaline promoters; (IV) catalysts containing Cu, ZnO, $Cr_2O_3$ activated with alkaline promoters; (V) catalysts containing Cu and Zn, Cr, Mn, Ca, Pb, Al, Th, etc. oxides (or salts) activated with alkaline metals; (VI) catalysts containing cobalt.

In paragraph (V) dealing with catalysts which may contain Cu, mention is made of catalyst Cu:Cr:K=1:4:1.97 which at a (high) temperature of 490° C. would yield, it is true, much isobutanol (37%), but which would suffer from the serious drawback of an extremely low resistance to ageing. The only other two catalysts mentioned, containing Cu, are: the catalyst according to U.S. Pat. No. 1,770,165 (ZnO-CuO-$K_2O$) and that according to German Pat. No. 565.309 ($K_2CO_3$, $V_2O_5$ and CuO in equal parts in weight) which would yield, however, at 480° C., 40% of MeOH, 25% of isobutanol, 20% of $H_2O$ and 15% of other higher and ester alcohols.

In the conclusions, catalysts based on ZnO seem to be preferred, while catalysts substantially based on Cu are ignored or, at least, not recommended.

To conclude, conventional catalysts most suitable for use seem to suffer from at least one of the following drawbacks: (a) they are difficult to manufacture and involve expensive basic components; (b) the alcohol mixtures they produce have a high methanol content and a relatively low higher alcohol content; (c) they may require high synthesis temperatures and involve, therefore, far from negligible energy costs; (d) they have a very short life.

The first object of this invention is now to produce a catalyst free from the above-mentioned drawbacks, which should also be easy to produce from inexpensive elements and should yield mixtures rich in higher alcohols.

Another object of the invention is a catalyst which should not only be easily prepared from inexpensive elements and should yield mixtures rich in higher alcohols, but should also operate at relatively low temperatures, with very interesting yields.

Another purpose of the invention is a particularly simple and advantageous process for preparing the catalysts in question.

Finally, yet another object of the invention is the advantageous application of said catalysts for preparing alcohol mixtures to be used as or with fuel.

These and other objects are achieved with the catalysts according to the invention, characterized by the fact that they are based on the following formula: $Cu-Ti_aM_bA_c$, in which Cu is copper, Ti is titanium, M is at least one metal from the group consisting of chrome, manganese, cobalt, molybdenum, rhodium, platinum and/or iron, A is an alkali metal or alkaline earth metal, and a, b, and c indicate molar proportions (referred to Cu) comprised respectively within the following intervals:

$a=0.1-0.5$, $b=0-0.2$, and $c=0-0.2$.

The alkali metal or alkaline earth metal is chosen preferably from potassium, lithium, magnesium or calcium.

In a preferred embodiment M is chrome, iron and/or manganese, A is potassium or calcium, b is comprised within 0.01 and 0.18 and c is comprised within 0.01 and 0.18.

The process for the preparation of the catalyst according to the invention is characterised by the fact that copper, titanium, and graphite powders are mixed, possibly, with an alkali metal salt or alkaline earth metal salt and acid salt from a metal preferably chrome, iron and/or manganese, the mixture is ground to fine particles in an inert ambient, the fine powder so obtained is compressed into pellets and the pellets so obtained undergo at least one heat treatment in argon at between 700° C. and 1100° C., and oxidation with argon and oxygen at 350° C.–500° C.

Metal M and metal A may possibly be added as oxides, hydrates or carbonates.

The mixture is preferably ground finely enough to transform it one hundred percent into fine particles 325–400 mesh. Of particular interest is the application of the catalyst in question for preparing in a variety of versions alcohol mixtures from synthesis gas: advantageously, these mixtures will contain alcohol from $C_1$ to $C_4$ when "b" when "c" are zero, and about 50% of alcohol from $C_1$ to $C_4$ and alcohol from $C_5$ to $C_{10}$ for the other 50% when "b" and "c" are other than zero.

These and other advantageous aspects of the invention will be better illustrated by the following non-limitative examples.

EXAMPLE 1

Ti/Cu Catalyst

To 479.02 g of Ti and 2286 g of Cu in the metallic powder state, are added 27.6 g of graphite powder.

Once weighed the powders are placed in a ball mill where they are finely pulverized, closely mixed. Granulometric analysis of the powders treated in a mill showed a 100% 325-400 mesh granulometry.

The closely mixed powder is compressed into 10×10 mm pellets, and the latter undergo the following treatments in a smelting furnace with the characteristics described below:

(1) treatment at 850° C. in an argon ambient keeping the powder at this temperature for an hour; (2) subsequently the powder is left to cool in the same furnace in an argon ambient down to a temperature of 400° C.; (3) at the above temperature of 400° C., the pellets were treated with an argon stream containing 0.1-0.2% of $O_2$ for two hours and (4) were subsequently treated with argon containing ever-increasing amounts of $O_2$ until the $O_2$ is 100%. This second oxidation phase lasted 3 hours.

The catalyst obtained in the oxidized state, consisting of $TiO_2/CuO$, is left to cool in a stream of $O_2$. The product taken from the furnace was in the shape of pellets with a tensile stress of 800 Kg/cm$^2$ and pouring density of 2.3 Kg/liter.

The furnace used for the above treatment was a smelting furnace in which heating energy was supplied in the form of electric power by exploiting the Joule effect: it consisted, in substance, of a tubular body to the ends of which were connected the terminals of a transformer's secondary to apply the required difference in tension for bringing the pellets to the desired temperature. (Similar results were obtained using other types of furnace, such as, for example, arc furnaces in inert ambient). Dimensions of the furnace used:

External tube diameter: 35 mm
Internal tube diameter: 32 mm
Axial tube length: 1190 mm The volume of catalyst treated in the form of 10×10 pellets was 600 cc. A tension of 220 V with a 50 Hz frequency was applied to the transformer's primary circuit.

The tension on the transformer's secondary circuit was 0-15 V and operating conditions for the treatments described above were as follows:

| Volt | Ampere | Time | Temperature ° C. |
|------|--------|------|------------------|
| 5.8  | 800    | —    | —                |
| 6.5  | 750    | 5'   | 164              |
| 6.8  | 670    | 15'  | 748              |
| 6.8  | 670    | 60'  | 850              |
| 6.8  | 670    | 120' | 850              |
| 3    | 350    | 150' | 400              |
| 3    | 350    | 450' | 400              |

With a copper and titanium alloy, treatment at 850° C. is equal to sintering (incipient smelting) which may last between one and three hours. The treatment at 400° C. is an oxidation which lasts about five hours.

Under these conditions a catalyst was obtained consisting of oxides in which metals were present in the following relative (with respect to copper) proportions:

CuTi0.28

EXAMPLE 2

A catalyst Cu/Ti/Cr/K was prepared proceeding as in Example 1, namely mixing 479 g of titanium, 2286 g of copper, 256 g of potassium ($K_2Cr_2O_7$) and 30.2 g of graphite.

After milling, pelletizing, treating in a furnace at 850° C. in argon (actual smelting) and subsequently oxidizing in the same furnace at 400° C., as in Example 1, a catalyst was obtained (CAT. 2) consisting of oxides in which metals were present in the following relative proportions:

CuTi0.28 Cr0.05 K0.05

EXAMPLE 3

A catalyst Cu/Ti/Cr/K was prepared, with the same amount of Ti (479 g) and of Cu (2286 g) as in example 1, but adding 28.9 g of graphite and a reduced amount of potassium bichromate which is now 129.5 g (as against 256 g in Example 2).

After milling, pelletizing, treating in a smelting furnace at 850° C. in argon (actual smelting) and subsequently oxidizing at 400° C. in argon and oxygen, as in Example 1, a catalyst was obtained (CAT. 3) consisting of oxides in which metals are in the following molar proportions:

CuTi0.28 Cr0.025 K0.025

EXAMPLE 4

A catalyst Cu/Ti/Cr/Ca was prepared mixing the same initial quantities of Ti (479 g), Cu (2286 g) and graphite (31.3 g) with 374 g of calcium bichromate ($CaCr_2O_7$).

After milling, pelletizing, treating in a furnace and oxidizing as in the preceding Examples, a catalyst (CAT. 4) was obtained consisting of oxides in which metals were in the following molar proportions:

CuTi0.28 Cr0.08 Ca0.04

EXAMPLE 5

A catalyst Cu/Ti/Mn/K was prepared by mixing 479 g of Ti, 2000 g of Cu, 32.8 g of graphite, and 805 g of potassium permanganate ($KMnO_4$).

Operating as in the preceeding Examples, a catalyst (CAT. 5) was obtained having the following composition:

CuTi0.32 Mn0.16 K0.16

EXAMPLE 6

A catalyst Cu/Ti/Cr/Co/K was prepared by mixing 479 g of Ti, 2000 g of Cu, 286 g of Co, 256 g of $K_2Cr_2O_7$ (potassium bichromate) and 30.2 g of graphite.

Operating as in the preceeding Examples, a catalyst (CAT. 6) was obtained with the following compositions:

CuTi0.32 Cr0.006 Co0.15 K0.05

EXAMPLE 7

A catalyst of the type described in Example 6 was prepared by mixing 479 g of Cu, 2000 g of Ti, 286 g of Co, 256 g of $K_2Cr_2O_7$, and 30.2 g of graphite. By operating as in Example 1, a catalyst (CAT. 7) was obtained having the following composition:

TiCu0.18 Cr0.04 Co0.11 K0.04

EXAMPLE 8

A catalyst Cu/Ti/Fe/Co/K was prepared by mixing, as in Example 1, 479 g of Ti, 1744 g of Cu, 138.6 g $(COO)_2Fe_2H_2O$ (ferrous oxalate), 286 g of Co, 228.4 g of potassium acetate and 28.7 g of graphite.

By operating as in Example 1, a catalyst (CAT. 8) was obtained having the following composition:

CuTi0.36 Co0.17 K0.08 Fe0.028

EXAMPLE 9

Catalyst Cu/Ti, CAT. 1 in Example 1, was used for the synthesis of mixtures of higher alcohols operating under the following experimental conditions:

| pressure | = | 60 Kg/cm$^2$ |
| --- | --- | --- |
| temperature | = | 340° C. |
| space velocity (VS) | = | 4000 H$^{-1}$ |
| volume of catalyst | = | 6 cc |
| size | = | 0.75–1 mm |

Composition of the feed gas was:

| % CO | 19.16 |
| --- | --- |
| % $CO_2$ | 9.38 |
| % $H_2$ | 62.48 |
| % $N_2$ | 8.98 |

A mixture of alcohols was obtained (with an extrapolated productivity equal to about 110 Kg/m$^3$cat/h) which under gas-chromatographic analysis showed the following composition (percentage in weight):

| Methyl alcohol ($C_1$) | 28.4% wt |
| --- | --- |
| Ethyl alcohol ($C_2$) | 38.6% wt |
| Isopropyl alcohol ($C_3$) | 3.8% wt |
| Normal propyl alcohol ($C_3$) | 18.5% wt |
| Secondary butyl alcohol ($C_4$) | 1.65% wt |
| Alcohols $C_5$–$C_{10}$ | 9.00% wt |

This shows that alcohols $C_1$ to $C_4$ are definitely preponderant, alcohols either $C_5$ or above $C_5$ being slightly less than 10%.

EXAMPLE 10

Catalyst Cu/Ti/Cr/K from Example 2 (CAT. 2) was used for the synthesis of higher alcohols mixtures, operating under the following experimental conditions (the same, in effect, as in Example 6):

| pressure | = | 60 Kg/cm$^2$ |
| --- | --- | --- |
| temperature | = | 340° C. |
| space velocity (VS) | = | 4000 H$^{-1}$ |
| volume of catalyst | = | 6 cc |
| size | = | 0.75–1 mm |

Composition of the feed gas was now as follows:

| % CO | 17.01 |
| --- | --- |
| % $CO_2$ | 5.89 |
| % $H_2$ | 71.39 |
| % $N_2$ | 5.71 |

A mixture of alcohols was obtained (with an extrapolated productivity of about 140 Kg/m$^3$ cat/h) which under gas-chromatographic analysis showed the following composition (percentage in weight):

| Methyl alcohol ($C_1$) | 14.19% wt |
| --- | --- |
| Ethyl alcohol ($C_2$) | 6.61% wt |
| Isopropyl alcohol ($C_3$) | 11.87% wt |
| N—propyl alcohol ($C_3$) | 8.47% wt |
| Secondary butyl alcohol ($C_4$) | 6.23% wt |
| Alcohols $C_5$–$C_{10}$ | 52.61 |

This shows that with a catalyst Cu/Ti/Cr/K an alcohol mixture is obtained which characteristically consists of about 50% in weight alcohols $C_1$ to $C_4$ and 50% in weight alcohols $C_5$ to $C_{10}$.

EXAMPLE 11

Catalyst Cu/Ti/Cr/K as in Example 3 was used for the synthesis of higher alcohols mixtures, operating under the following experimental conditions:

| pressure | = | 60 Kg/cm$^2$ |
| --- | --- | --- |
| temperature | = | 340° C. |
| space velocity (VS) | = | 4000 H$^{-1}$ |
| volume of catalyst | = | 6 cc |
| size | = | 0.75–1 mm |

Composition of the feed gas was:

| % CO | 19.3 |
| --- | --- |
| % $CO_2$ | 8.2 |
| % $H_2$ | 68.0 |
| % $N_2$ | 4.5 |

The gas-chromatographic analysis of the mixture so obtained (with a productivity of about 120 Kg/m$^3$ cat./h) showed the following composition:

| Methyl alcohol ($C_1$) | 22% in weight |
| --- | --- |
| Ethyl alcohol ($C_2$) | 20% in weight |
| Isopropyl alcohol ($C_3$) | 5% in weight |
| Propyl alcohol ($C_3$) | 13% in weight |
| Secondary butyl alcohol ($C_4$) | 22% in weight |
| Alcohols $C_5$–$C_{10}$ | 18% in weight |

EXAMPLE 12

Catalyst Cu/Ti/Mn/K (CAT. 5) as in Example 5 was used, under the same operating conditions and with a feed gas stream as in Example 7. The chromatographic analysis of the product obtained (with a yield of about 110 Kg/m$^3$ cat./h) showed the following composition (weight percentages):

| Methyl alcohol ($C_1$) | 10% wt |
| --- | --- |
| Ethyl alcohol ($C_2$) | 4.3% wt |
| Isopropyl alcohol ($C_3$) | 8.2% wt |
| Normal propyl alcohol ($C_3$) | 9.5% wt |
| Secondary butyl alcohol ($C_4$) | 12% wt |
| Alcohols $C_5$–$C_{10}$ | 55% wt |

EXAMPLES 13–15

Catalysts Cu/Ti/Cr/Co/K of Example 6 (CAT. 6) and of Example 7 (CAT. 7) and catalyst Cu/Ti/Fe/Co/K (CAT. 8) of Example 8 were used under the same operating conditions and with the same feed gas stream of Example 7.

The composition of the products obtained was:

|  | CAT. 6 | CAT. 7 | CAT. 8 |
| --- | --- | --- | --- |
| $C_1$ | 36% by weight | 33% by weight | 32% by weight |
| $C_2$ | 30% by weight | 32% by weight | 31% by weight |
| $C_3$ (Total) | 21% by weight | 22% by weight | 22% by weight |
| $C_4$ | 8.5% by weight | 8% by weight | 10% by weight |
| $C_5-C_{10}$ | 3.5 by weight | 4% by weight | 4% by weight |

I claim:

1. A catalyst for the preparation of alcohol mixtures rich in alcohols higher than methanol from a synthesis gas containing $H_2$, CO, and $CO_2$, consisting essentially of an oxidized alloy of metals according to the formula $$CuTi_aM_bA_c$$

wherein Cu is copper, Ti is titanium, M is at least one metal selected from the group consisting of chromium, manganese, cobalt, molybdenum, rhodium, platinum, and iron, and A is an alkali metal or an alkaline earth metal;

wherein a is 0.1 to 0.5; b is 0.01 to 0.18; and c is 0.01 to 0.18; and a, b, and c represent the molecular proportions of Ti, M, and A, respectively, to Cu; and wherein each of the metals is present in the catalyst in the form of an oxide.

2. The catalyst of claim 1, wherein A is potassium, lithium, magnesium, or calcium.

3. The catalyst of claim 1, wherein M is chromium or manganese and A is potassium or calcium.

4. A process for the production of the catalyst of claim 1 comprising
   (a) admixing copper, titanium, an oxide, hydrate or a salt of the metal A, an oxide, hydrate or an acid salt of the metal M, and graphite powder;
   (b) grinding the admixed metals and graphite to a fine powder in an inert, ambiant atmosphere;
   (c) compressing the fine powder into pellets;
   (d) heat treating the pellets at least once in argon at a temperature between 700° C. and 1100° C.; and
   (e) oxidizing the heat-treated pellets with argon and oxygen at a temperature between about 350° C. to about 500° C.

5. The process of claim 4, wherein the metals A and M are admixed in the form of their carbonates in step (a).

6. The process of claim 4, wherein the metal M is chromium or manganese.

7. The process of claim 4, wherein the fine powder obtained in step (b) has a particle size of from 325 to 400 mesh.

8. The process of claim 4, wherein the metal A is added in the form of a salt of an acid of the metal M.